United States Patent
Okawa

(10) Patent No.: US 7,662,640 B2
(45) Date of Patent: Feb. 16, 2010

(54) METHOD FOR SILVER STAINING OF BIOLOGICAL SUBSTANCES

(75) Inventor: Asako Okawa, Kyoto (JP)

(73) Assignee: Kyoto University, Kyoto (JP)

( * ) Notice: Subject to any disclaimer, the term of this patent is extended or adjusted under 35 U.S.C. 154(b) by 488 days.

(21) Appl. No.: 11/663,632

(22) PCT Filed: Sep. 27, 2005

(86) PCT No.: PCT/JP2005/017769
§ 371 (c)(1),
(2), (4) Date: Mar. 23, 2007

(87) PCT Pub. No.: WO2006/035781
PCT Pub. Date: Apr. 6, 2006

(65) Prior Publication Data
US 2007/0292961 A1 Dec. 20, 2007

(30) Foreign Application Priority Data
Sep. 28, 2004 (JP) ............... 2004-282227

(51) Int. Cl.
*G01N 1/30* (2006.01)
(52) U.S. Cl. .............. 436/174; 436/8; 436/80; 436/86; 436/164; 436/166; 436/169; 436/905; 435/6; 204/456; 204/462
(58) Field of Classification Search .......... 436/8, 436/80, 164, 166, 169, 174, 905; 435/6; 204/456, 462
See application file for complete search history.

(56) References Cited

U.S. PATENT DOCUMENTS 5,064,768 A  11/1991  Ebata et al.
5,492,810 A   2/1996  Caetano-Anolles et al.

FOREIGN PATENT DOCUMENTS

JP       02-080958       3/1990

OTHER PUBLICATIONS

English language Abstract of JP 02-080958.
M. Swain et al., Electrophoresis, 1995, vol. 16, pp. 948-951.
F. Zalazar et al., Analytical Biochemistry, 2001, vol. 291, pp. 299-300.
A. Shevchenko et al., Anal. Chem., 1996, vol. 68, pp. 850-858.
J. X. Yan et al., Electrophoresis, 2000, vol. 21, pp. 3666-3672.

*Primary Examiner*—Robert J Hill, Jr.
*Assistant Examiner*—Dwan A Gerido
(74) *Attorney, Agent, or Firm*—Greenblum & Bernstein, P.L.C.

(57) ABSTRACT

A method for silver staining a gel on which biological substances such as nucleic acids and proteins are separated by electrophoresis, which comprises at least the following steps: (a) the step of immersing an untreated gel after the electrophoresis in an aqueous solution of sodium thiosulfate; (b) the step of immersing the gel obtained in the step (a) in a mixture of ethanol and an aqueous solution of sodium acetate; and (c) the step of immersing the gel obtained in the step (b) in a mixture of ethanol and an aqueous solution of silver nitrate.

7 Claims, 2 Drawing Sheets

METHOD FOR SILVER STAINING OF BIOLOGICAL SUBSTANCES

FIELD OF THE INVENTION

The present invention relates to a method for silver staining of a biological substance such as a protein or nucleic acid.

BACKGROUND OF THE INVENTION

Since development of sodium dodecylsulfate polyacrylamide gel electrophoresis (SDS-PAGE), PAGE has become an indispensable means in the biochemical analyses of biosamples such as proteins and nucleic acids. As a means for detecting proteins on a polyacrylamide gel after electrophoresis, for example, the CBB staining, silver staining, fluorescent staining, and the like can be used. In comprehensive researches for analyzing entire features of proteins (proteome) in a biological tissue or cell to facilitate developments of pharmaceuticals, i.e., proteomics, a particularly high sensitive means is desired, and among the aforementioned means, the silver staining has been widely used in this field as a method that can provide the highest detection sensitivity without need of any special detection apparatus. When silver staining is performed by using a commercially available silver staining kit or the like currently provided, detection at a protein amount of several hundreds picograms or more is achievable.

However, even when a conventional silver staining method is used, $10^8$ to $10^9$ or more cells are required to detect a protein of which expression amount per cell is low. If recovery efficiency of the protein is taken into consideration, much more numbers of cells are required, and thus a problem arises that practical analysis is impossible. Under the circumstances, it is strongly desired to develop a method which is capable of clearly visualizing a protein on a gel even when PAGE is performed by using a small amount of the protein, for example, about several tens picograms.

DISCLOSURE OF THE INVENTION

Object to be Achieved by the Invention

An object of the present invention is to provide a method for detecting a biological substance on a gel such as polyacrylamide gel after electrophoresis with high sensitivity. More specifically, the object of the present invention is to provide a method for detecting a biological substance on a gel such as polyacrylamide gel after electrophoresis with extremely high sensitivity by silver staining.

Means for Achieving the Object

The inventor of the present invention conducted various researches to achieve the aforementioned object, and as a result, found that a biological substance was successfully detected with extremely high sensitivity by performing silver staining according to the following steps.

The present invention thus provides a method for silver staining of a gel on which a biological substance is separated by electrophoresis, which comprises at least the following steps:
(a) the step of immersing an untreated gel after the electrophoresis in an aqueous solution of sodium thiosulfate;
(b) the step of immersing the gel obtained in the aforementioned step (a) in a mixture of ethanol and an aqueous solution of sodium acetate; and
(c) the step of immersing the gel obtained in the aforementioned step (b) in a mixture of ethanol and an aqueous solution of silver nitrate.

According to a preferred embodiment of the aforementioned invention, there is provided the aforementioned method, wherein, in the step (c), the gel obtained in the step (b) is immersed in a mixture of ethanol and an aqueous solution of silver nitrate without washing the gel with water.

According to a more preferred embodiment, there is provided a method for silver staining of a gel on which a biological substance is separated by electrophoresis, which comprises at least the following steps:
(a) the step of immersing an untreated gel after the electrophoresis in an aqueous solution of sodium thiosulfate;
(a-2) the step of immersing the gel obtained in the aforementioned step (a) in a mixture of ethanol and an aqueous solution of acetic acid;
(b') the step of immersing the gel obtained in the aforementioned step (a-2) in a mixture of ethanol and an aqueous solution of sodium acetate; and
(c') the step of immersing the gel obtained in the aforementioned step (b') in a mixture of ethanol and an aqueous solution of silver nitrate without washing the gel with water.

In the aforementioned method, for example, a polyacrylamide gel or agarose gel can be used as the gel, and a polyacrylamide gel can be preferably used.

From another aspect, the present invention provides a kit for performing the aforementioned method. This kit includes a combination of the reagents used in the steps of the aforementioned method.

EFFECT OF THE INVENTION

By performing silver staining according to the method of the present invention, a biological substance separated by gel electrophoresis can be detected with extremely high sensitivity. In the method of the present invention, use of formalin in the silver staining step can be reduced as low as possible, and thus a biological sample contained in a gel after the staining is unlikely subjected to chemical modification. Therefore, the method of the present invention also has an advantage that the biological sample after the staining can be more precisely analyzed by using a mass spectrometer.

BEST MODE FOR CARRYING OUT THE INVENTION

Figure 1:
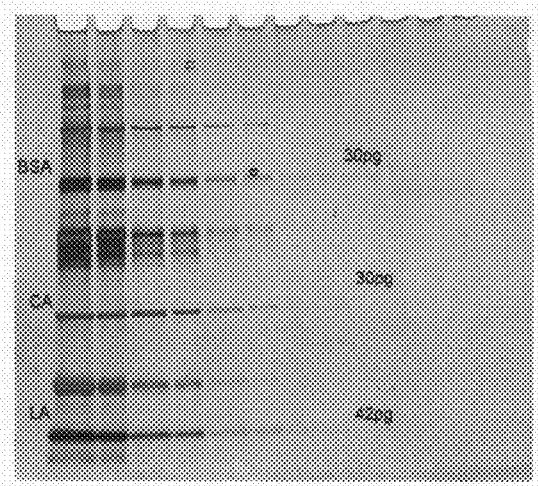
[FIG. 1] Photograph of the polyacrylamide silver stained in Example 1. BSA represents albumin, CA represents carbonic anhydrase, LA represents α-lactalbumin, and the numbers in the photograph represent the minimum amounts of the proteins detected.

The method of the present invention is for silver staining of a gel on which a biological substance is separated by electrophoresis, and comprises at least the aforementioned steps (a), (b), and (c), and according to a preferred embodiment, the method comprises the aforementioned steps (a), (a-2), (b'), and (c'). In the specification, the term "biological substance" means a polymer substance that constitutes a living body, and more specifically, examples include nucleic acids (including DNA and RNA), proteins, and the like, which can be separated and detected by gel electrophoresis. However, the substances are not limited to these examples. Further, the biological substance is not limited to naturally occurring substances, and the term should be construed in the broadest sense including non-naturally occurring type nucleic acids, proteins newly created by a genetic engineering technique, and the like. The methods of separating biological substances by polyacrylamide gel electrophoresis, agarose gel electrophoresis, and the like are widely used in this field, and for the method of the present invention, an arbitrary type of gel can be used. Examples of the gel include, for example, an agarose gel, polyacrylamide gel, and the like, and a polyacrylamide gel is preferably used. Agarose gels or polyacrylamide gels of various concentrations can be chosen and used depending on the type of the biological substance. The method of electrophoresis is not also particularly limited in the method of the present invention.

The step (a) is to immerse an untreated gel after electrophoresis in an aqueous solution of sodium thiosulfate (step of sensitization 1). This step is performed to prevent a band of a protein stained on the gel from whitely clouding and to provide a clear band. According to a standard procedure that is adopted by marketed silver staining kits, this step has conventionally been performed immediately before the staining step by immersion in an aqueous solution of silver nitrate and the like. However, as a result of researches by the inventor of the present invention, it was found that if a gel was not sufficiently washed with water or the like after the immersion in an aqueous solution of sodium thiosulfate when the conventional step was employed, a problem arose that background was stained, and thus satisfactory detection sensitivity of a protein by the staining was not obtainable.

In the method of the present invention, the step of immersing an untreated gel, obtained immediately after performing electrophoresis, in an aqueous solution of sodium thiosulfate is employed, and then the gel is subjected to the step (a-2) (fixation step) and (b) or (b') (step of sensitization 2), thereby staining of the background is suppressed, and the sensitization effect obtainable by the immersion in an aqueous solution of sodium thiosulfate can be fully exhibited. In the step (a), although concentration of sodium thiosulfate in the aqueous solution of sodium thiosulfate is not particularly limited, the concentration is preferably, for example, about 0.02%. Although the immersion time is also not particularly limited, the time is usually preferably about 2 minutes. Use of a higher sodium thiosulfate concentration and longer immersion time may sometimes result in staining of the background.

Following the aforementioned step (a), the step of immersing the gel obtained in the step (a) in a mixture of ethanol and an aqueous solution of sodium acetate can be performed (step (b), step of sensitization 2). Prior to this step (b), the step of immersing the gel obtained in the step (a) in a mixture of ethanol and an aqueous solution of acetic acid (step (a-2), fixation step) may optionally be added, and it is generally desirable to employ this fixation step. Following the step (a-2) in this option, the gel obtained in the step (a-2) may be immersed in a mixture of ethanol and an aqueous solution of sodium acetate (step (b')).

In the fixation step by immersion of the gel in a mixture of ethanol and an aqueous solution of acetic acid, although a concentration of ethanol in the mixture is not particularly limited, the concentration is preferably, for example, about 40% by weight based on the total weight of the mixture. Although a concentration of acetic acid in the mixture is not particularly limited, the concentration is preferably, for example, about 10% by weight. In order to attain sufficient fixation of proteins, the immersion period of time in the fixation step is preferably 30 minutes or longer, and the immersion is preferably performed two or more times with appropriately exchanging the mixture of ethanol and an aqueous solution of acetic acid. It is especially preferred that the immersion is performed twice for an immersion time of 30 minutes. Although the immersion time of the fixation step may be a longer time (for example, overnight), immersion for an unnecessarily long time may sometimes result in degradation of detection sensitivity for proteins of low molecular weights.

In the step of sensitization 2 in which the gel is immersed in a mixture of ethanol and an aqueous solution of sodium acetate, although a concentration of ethanol in the mixture is not particularly limited, the concentration is, for example, preferably about 20 to 40% by weight, more preferably 30% by weight, based on the total weight of the mixture. Although a concentration of sodium acetate in the mixture is not particularly limited, the concentration is preferably, for example, about 0.5 to 1.0 M. With a concentration lower than 0.5 M or higher than 1.0 M, sufficient sensitization effect may be sometimes not obtained. Further, although the immersion time in the mixture in the step of sensitization 2 is preferably 30 minutes or longer, immersion for a unnecessarily prolonged time may sometimes degrade detection sensitivity for proteins of low molecular weights.

Subsequently, the step of immersing the gel obtained in the step (b) or (b') in a mixture of ethanol and an aqueous solution of silver nitrate (staining step) is performed. In the methods reported so far in articles (Schevchenko A et al., Anal. Chem., 68, pp. 850-858, (1996) and the like) and the methods employed in marketed silver staining kits, a step of washing a gel with water or the like is adopted between the step of sensitization 2 for treatment of the gel with sodium acetate and the staining step for treatment with silver nitrate. However, as a results of researches by the inventor of the present invention, it was found that, if washing with water or the like was performed between the step of sensitization 2 and the staining step, such problems arose that detection sensitivity for low molecular weight proteins was lowered. According to a preferred embodiment of the method of the present invention, the gel obtained in the step of sensitization 2 (step (b) or step (b')) is subjected to the staining step without washing the gel with water, thereby the sensitization effect for detection sensitivity obtained in the step of sensitization 2 can be fully exhibited, and thus the detection sensitivity for low molecular weight proteins is also sufficiently maintained.

In the conventional silver staining methods, a step of immersing the gel in an aqueous solution of silver nitrate, a mixed aqueous solution of silver nitrate and formalin, a mixed aqueous solution of silver nitrate and sodium thiosulfate, or the like is employed for the staining step. However, if an aqueous solution of silver nitrate alone is used, staining property is insufficient, and if an aqueous solution of silver nitrate and formalin is used, proteins may be chemically modified by the aldehyde, although staining property is improved. Therefore, there is a problem that use of formalin should be avoided as much as possible when analysis is performed by using a mass spectrometer. Further, a mixed aqueous solution of silver nitrate and sodium thiosulfate has a problem that it causes degradation of staining due to structural change of a gel. As a result of researches by the inventor of the present invention, it was found that staining of background of a gel was successfully suppressed, and bands of stained proteins were clarified to attain improvement of detection sensitivity by addition of ethanol to the aqueous solution of silver nitrate.

In the staining step, although a concentration of ethanol in the mixture of ethanol an aqueous solution of silver nitrate is not particularly limited, the concentration is, for example, about 15 to 20% by weight, more preferably 20% by weight, based on the total weight of the mixture. Further, a concentration of silver nitrate in the mixture is preferably about 0.2 to 0.3% by weight, more preferably 0.25% by weight, based on the total weight of the mixture. An immersion time in the staining step is preferably about 15 to 20 minutes. If the immersion time is unnecessarily prolonged, excessive silver ions may be sometimes not washed out in the subsequent washing step, which may sometimes result in staining of background.

As explained above, the method of the present invention uses a mixed solution containing ethanol and water in the aforementioned steps (a-2), (b) (or (b')), and (c) (or (c')), and this is one of characteristic features of the present invention. Use of a mixture of methanol and water in a fixation step and/or a sensitization step was previously reported. However, as a result of researches by the inventor of the present invention, it was found that if methanol was used, a problem arose that staining became entirely palely, and thus detection sensitivity was degraded. It was also found as a result of researches by the inventor of the present invention that the aforementioned problem was successfully solved by use of ethanol instead of methanol. When a further higher alcohol was used, no significant difference in detection sensitivity was observed, but staining of background was tend to be deeper. Therefore, ethanol is most preferably used. In addition, a small amount of ethanol may be added in the step of sensitization 1 as the step (a). Although temperature for performing the aforementioned steps (a), (a-2), (b), (b'), (c), and (c') is not particularly limited, the temperature is preferably, for example, about 25° C.

Following the step (c), the step (d) for washing the gel obtained in the aforementioned staining step with water (washing step); the step (e) for immersing the gel obtained in the aforementioned washing step in an aqueous solution containing a mixture of sodium carbonate and formalin (development step); and the step (f) for immersing the gel obtained in the aforementioned step (e) in an acidic aqueous solution (development stopping step) can be performed to attain silver staining of the gel. The aforementioned steps (d) to (e) can be performed according to methods ordinarily used in this field.

The washing step is desirably performed in a period of time as short as possible but so as to sufficiently remove excessive silver ions. If the washing is insufficient, staining of background may sometimes be observed, and bands of proteins may be sometimes not detected. Specifically, it is preferable to repeat 2 or 3 times the step of immersion and shaking for 30 seconds to about 1 minute. In the development step, a concentration of sodium carbonate in the aqueous solution is preferably, for example, 2 to 3% by weight, more preferably 2.5% by weight. A concentration of formalin in the aqueous solution is preferably, for example, 0.04 to 0.06% by weight, more preferably 0.06% by weight. Although an immersion period of time in the development step can be suitably determined depending on proteins to be stained, it is usually about 1 to 10 minutes. If the immersion is performed for an unnecessarily prolonged time, proteins may be chemically modified by the aldehyde, and analysis by a mass spectrometer may sometimes become impossible. Type of the acid used in the development stop step is not particularly limited, and ordinarily used mineral acids, organic acids such as acetic acid, and the like can be appropriately used. For example, when an aqueous solution of acetic acid is used as the acidic aqueous solution, a concentration of acetic acid of, for example, 1% by weight or more is sufficient.

It is also possible to automate the method of the present invention, and it should be understood that an automated silver staining apparatus for performing a silver staining method comprising at least the aforementioned steps (a), (b) and (c), preferably an automated silver staining apparatus for performing a silver staining method comprising at least the aforementioned steps (a), (a-2), (b') and (c'), and the like fall within the scope of the present invention. Furthermore, an automated silver staining apparatus for performing a silver staining method further comprising the aforementioned steps (d) and (e) in addition to the aforementioned steps (a), (b) and (c) also falls within the scope of the present invention. Further, the kit provided by the present invention is that provided comprising at least two or more types of reagents among the regents used in the aforementioned step (a), (b), and (c). For example, a combination of two or more kinds of reagents selected from the group consisting of sodium acetate, sodium thiosulfate, and silver nitrate, and the like are preferred. Further, this combination of reagents may be provided as a combination further comprising ethanol and/or acetic acid. Furthermore, the combination may be provided as a combination also comprising sodium carbonate and formalin used in the step (e).

EXAMPLES

The present invention will be explained more specifically with reference to examples. However, the scope of the present invention is not limited to the following examples.

Example 1

Commercially available markers (LMW Marker, Amersham Bioscience), of which amounts as proteins were calculated, were added to a commercially available 15% polyacrylamide gel (Bio Craft), and subjected to electrophoresis at a constant current of 20 mA. As the sample buffer, a commercially available buffer containing mercaptoethanol (Daiichi Pure Chemicals) was used. After the electrophoresis, the polyacrylamide gel was immediately immersed in a 0.02% aqueous solution of sodium thiosulfate for 2 minutes, then immersed in a 40% ethanol/10% acetic acid mixed aqueous solution twice for 30 minute for each time, immersed in a 30% ethanol/0.5 M sodium acetate mixed aqueous solution for 30 minutes, and further immersed in a 20% ethanol/0.25% silver nitrate mixed aqueous solution for 20 minutes to perform silver staining. Development and cease of the development were performed by washing the polyacrylamide gel obtained above twice with water for 1 minute for each time, and immersing the gel in a 2.5% sodium carbonate/0.06% formalin mixed aqueous solution for 6 minutes, and then in a 1% aqueous solution of acetic acid for 5 minutes. A photograph of the resulting polyacrylamide gel is shown in FIG. 1. In the photograph, BSA represents albumin, CA represents carbonic anhydrase, and LA represents α-lactalbumin. The numbers in the photograph represents the minimum amounts of the proteins detected, and they were 30 pg for BSA, 30 pg for CA, and 42 pg for LA. The amounts of BSA and CA added to the lanes in the photograph were 100 ng, 50 ng, 10 ng, 5 ng, 1 ng, 500 pg, 100 pg, 50 pg, 30 pg, 10 pg, 5 pg, and 3 pg from the left, and the amounts of LA were similarly 140 ng, 70 ng, 14 ng, 7 ng, 1.4 ng, 700 pg, 140 pg, 70 pg, 42 pg, 14 pg, 7 pg, and 4.2 pg.

Example 2

Commercially available carbonic anhydrase (CA, Sigma) was added in an amount of 1 μg per lane to a commercially available 15% polyacrylamide gel (Bio Craft), and subjected to electrophoresis at a constant current of 20 mA. As the sample buffer, a commercially available buffer containing mercaptoethanol (Daiichi Pure Chemicals) was used. After the electrophoresis, the polyacrylamide gel was immediately immersed in a 0.02% aqueous solution of sodium thiosulfate for 2 minutes, then immersed in a 40% ethanol/10% acetic acid mixed aqueous solution twice for 30 minute for each time, immersed in a 30% ethanol/0.5 M sodium acetate mixed aqueous solution for 30 minutes, and further immersed in a 20% ethanol/0.25% silver nitrate mixed aqueous solution for 20 minutes to perform silver staining. Development and cease of the development were performed by washing the polyacrylamide gel obtained above twice with water for 1 minute for each time, and immersing the gel in a 2.5% sodium carbonate/0.06% formalin mixed aqueous solution for 6 minutes, and then in a 1% aqueous solution of acetic acid for 5 minutes. A photograph of the resulting polyacrylamide gel is shown in FIG. 2(A).

Figure 2:
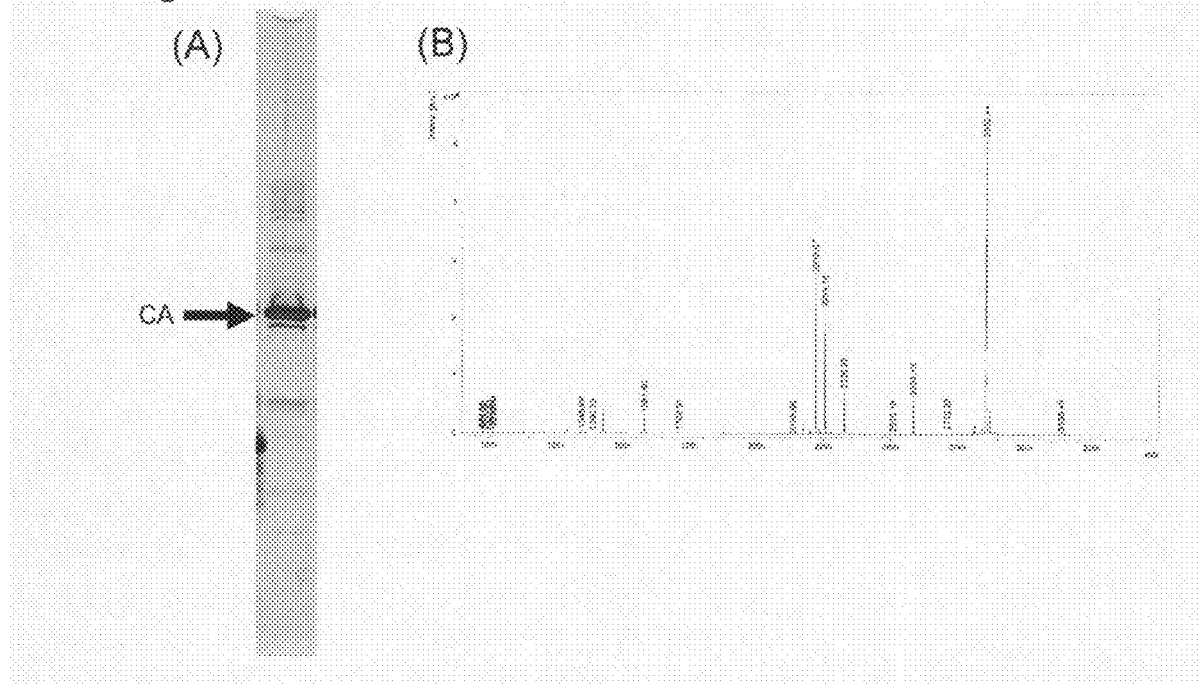
[FIG. 2] Photograph of the polyacrylamide gel silver stained in Example 2. In the photograph, the arrow in (A) represents the band of carbonic anhydrase. (B) shows a mass spectrometry spectrum of the band indicated with the arrow in (A).

The band indicated with an arrow in FIG. 2(A) was excised, decolorized with a 1:1 mixed aqueous solution of 100 mM sodium thiosulfate aqueous solution and 30 mM potassium hexacyanoferrate(III) aqueous solution, and washed several times with water. Water was eliminated, and the gel was minced in a size of about 1 mm$^3$, and dried to a solid. The resultant was treated overnight at 37° C. with a 50 mM ammonium bicarbonate and 2% acetonitrile aqueous solution (pH 8.0) containing a required amount of trypsin (Promega) to fragment the target protein. The fragmented peptides were extracted, desalted and concentrated by using a reverse phase resin filled pipet chip. A mass spectrometry spectrum obtained by analysis of the resulting fragmented peptides using a mass spectrometer (MALDI-TOF-TOF) is shown in FIG. 2(B). Proteins were searched in the spectrum (peptide mass fingerprinting method), and carbonic anhydrase was identified. The amino acid sequence covering ratio thereof was 74%.

Example 3 (Separation and Silver Staining of Nucleic Acids)

Figure 3:
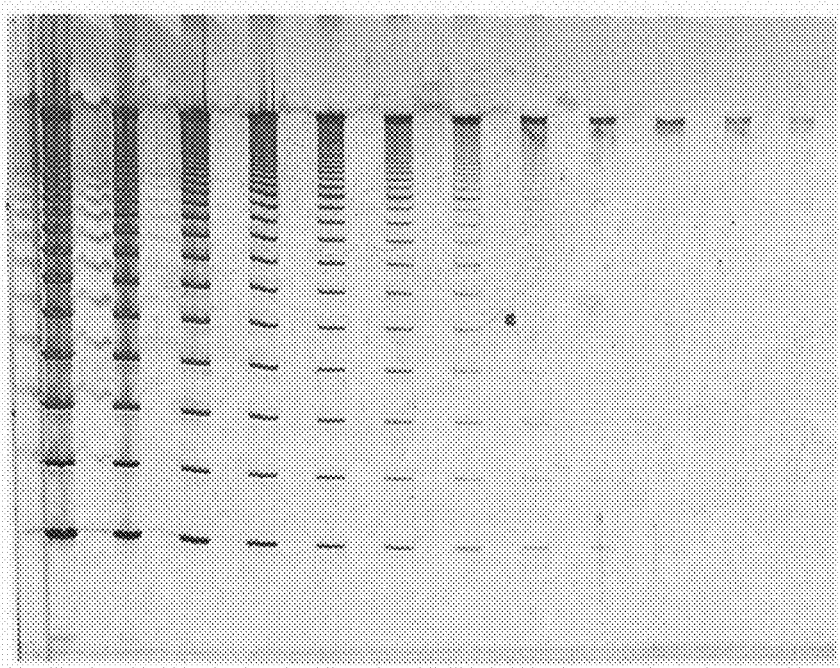
[FIG. 3] Photograph of the polyacrylamide gel silver stained in Example 3.

Commercially available markers (100 bp Ladder, Amersham Bioscience) were added to a commercially available 12.5% polyacrylamide gel (Amersham Bioscience), and subjected to electrophoresis at a constant current of 50 mA. As the sample buffer, a commercially available Tris-EDTA buffer (pH 7.5) was used. After the electrophoresis, the polyacrylamide gel was immediately immersed in a 0.02% aqueous solution of sodium thiosulfate for 2 minutes, then immersed in a 40% ethanol/10% acetic acid mixed aqueous solution twice for 30 minute for each time, immersed in a 30% ethanol/0.5 M sodium acetate mixed aqueous solution for 30 minutes, and further immersed in a 20% ethanol/0.25% silver nitrate mixed aqueous solution for 20 minutes. Development and development stop were performed by washing the polyacrylamide gel obtained above twice with water for 1 minute for each time, and immersing the gel in a 2.5% sodium carbonate/0.06% formalin mixed aqueous solution for 6 minutes, and then in a 1% aqueous solution of acetic acid for 5 minutes. A photograph of the resulting polyacrylamide gel is shown in FIG. 3. The amounts of the total nucleic acids added to the lanes in the photograph were 2.5 μg, 1.25 μg, 625 ng, 312.5 ng, 156.25 ng, 78.15 ng, 39.1 ng, 19.55 ng, 9.8 ng, 4.9 ng, 2.45 ng, and 1.25 ng from the left.

INDUSTRIAL APPLICABILITY

By performing silver staining according to the method of the present invention, biological substances separated by gel electrophoresis can be detected with extremely high sensitivity.

What is claimed is:

1. A method for silver staining of a gel on which a biological substance is separated by electrophoresis, which comprises at least the following steps:
    (a) the step of immersing an untreated gel after the electrophoresis in an aqueous solution of sodium thiosulfate;
    (b) the step of immersing the gel obtained in the step (a) in a mixture of ethanol and an aqueous solution of sodium acetate; and
    (c) the step of immersing the gel obtained in the step (b) in a mixture of ethanol and an aqueous solution of silver nitrate.

2. The method according to claim 1, wherein, in the step (c), the gel obtained in the step (b) is immersed in a mixture of ethanol and an aqueous solution of silver nitrate without washing the gel with water.

3. The method according to claim 1, which further comprises:
    (d) the step of washing the gel obtained in the staining step (c) or with water;
    (e) the step of immersing the gel obtained in the step (d) in an aqueous solution containing a mixture of sodium carbonate and formalin; and
    (f) the step of immersing the gel obtained in the step (e) in an acidic aqueous solution.

4. The method according to claim 1, wherein the gel is a polyacrylamide gel or an agarose gel.

5. The method according to claim 1, wherein the biological substance is a nucleic acid or a protein.

6. A method for silver staining a gel on which a biological substance is separated by electrophoresis, which comprises at least the following steps:
    (a) the step of immersing an untreated gel after the electrophoresis in an aqueous solution of sodium thiosulfate;
    (a-2) the step of immersing the gel obtained in the step (a) in a mixture of ethanol and an aqueous solution of acetic acid;
    (b') the step of immersing the gel obtained in the aforementioned step (a-2) in a mixture of ethanol and an aqueous solution of sodium acetate; and
    (c') the step of immersing the gel obtained in the step (b') in a mixture of ethanol and an aqueous solution of silver nitrate without washing the gel with water.

7. The method according to claim 6, which further comprises
    (d') the step of washing the gel obtained in the staining step (c') with water,
    (e') the step of immersing the gel obtained in the step (d') in an aqueous solution containing a mixture of sodium carbonate and formalin, and
    (f') the step of immersing the gel obtained in step (e') in an acidic aqueous solution.

* * * * *